US00PP33898P2

(12) United States Plant Patent
Coetzee

(10) Patent No.: US PP33,898 P2
(45) Date of Patent: Jan. 25, 2022

(54) GRAPEVINE PLANT NAMED 'NAVSEL 20'

(50) Latin Name: *Vitis vinifera*
Varietal Denomination: NAVSEL 20

(71) Applicant: Special New Fruit Licensing Limited, Peterborough (GB)

(72) Inventor: Gideon Jacobus Nicolaas Coetzee, Peterborough (GB)

(73) Assignee: Special New Fruit Licensing Limited, Peterborough (GB)

( * ) Notice: Subject to any disclaimer, the term of this patent is extended or adjusted under 35 U.S.C. 154(b) by 0 days.

(21) Appl. No.: 17/117,438

(22) Filed: Dec. 10, 2020

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 6/88
See application file for complete search history.

(56) References Cited

PUBLICATIONS

U.S. Appl. No. 17/117,451, filed Dec. 10, 2020, Coetzee.
T.R. Turoni Technical Bulletin, "53215 Durometer—pulp hardness tester (non-invasive)" Undated.
Steven C. Williams, "What is Durometer?—Elastomer and Plastic Hardness" Industrial Specialties Mfg. & IS MED Specialties, <https://www.industrialspec.com/about-US/blog/detail/what-is-durometer-elastomer-and-plastic-hardness> Accessed on Jun. 4, 2021.

*Primary Examiner* — Anne Marie Grunberg
(74) *Attorney, Agent, or Firm* — Dentons US LLP

(57) ABSTRACT

'NAVSEL 20' is a new and distinct grapevine plant with novel characteristics that include medium fertility and dark violet berries. The berries produced by 'NAVSEL 20' are seedless with a very crisp texture and no detectable seed traces. The berries produced by 'NAVSEL 20' are large, weighing 10 g/berry on average, and are harvested in July in Spain.

1 Drawing Sheet

Latin name of the genus and species of the plant claimed: *Vitis vinifera.*

Cultivar denomination: 'NAVSEL 20'.

BACKGROUND OF THE INVENTION

The present invention relates to a new distinct variety of seedless grapevine named 'NAVSEL 20'. The variety originated from a hybridization performed in Wellington in 2008, in South Africa between '9-762' (unpatented), as the pollen parent, and 'R5V38-44' (unpatented), as the seed parent in 2008. Abortive seed traces were embryo cultured and the resulting plant was planted in an evaluation block during 2009. The first evaluation of the fruit produced by 'NAVSEL 20' was performed during 2011. 'NAVSEL 20' was first asexually propagated by field grafting dormant hardwood scions to rootstock in 2013 in South Africa. Fruit from the resulting four grafted 'NAVSEL 20' vines was first harvested in 2015. All characteristics and distinctions remain true to form and are established and transmitted through succeeding propagations.

SUMMARY OF THE INVENTION

The following are the most outstanding and distinguishing characteristics of 'NAVSEL 20'. 'NAVSEL 20' produces large, dark violet (5RP 3/2), seedless berries that are harvested in late July, in Spain (Murcia Region), and weigh on average 10 g/berry.

The new cultivar is distinguished from its male parent, '9-762' in that NAVSEL 20 produces dark violet-coloured grapes while '9-762' produces green coloured grapes. Additionally, NAVSEL 20 berry shape is cylindrical compared to the ellipsoidal berry shape of 9-762. NAVSEL 20 has high vigour while 9-762 has medium vigour.

'NAVSEL 20' is believed to be most similar to 'R5V38-44'. Nonetheless, the new cultivar is distinguished from its female parent, 'R5V38-44' in that NAVSEL 20 berries are bigger than R5V38-44, and NAVSEL 20 berry shape is cylindrical compared to the globose berry shape of R5V38-44. NAVSEL 20 also has a thin skin while R5V38-44 has a thick skin.

Additionally, 'NAVSEL 20' is an early season cultivar harvested in July in the Murcia region in Spain, which is distinguishable from the later August harvest period of both '9-762' and 'R5V38-44'.

Similar to 'NAVSEL 20', 'NAVSEL 21' (U.S. patent application Ser. No. 17/117,451) is another grapevine variety that is an early season cultivar harvested in July. Nonetheless, plants of 'NAVSEL 20' and 'NAVSEL 21' can be readily and unambiguously distinguished from one another at least based upon their plant habit and growth, skin color, trunk characteristics, time of bud burst, skin color and floral clusters. For example, 'NAVSEL 20' exhibits a semi-erect growth habit, thinner trunk; later bud burst, 5RP 3/2 skin color and fewer inflorescences per cluster, whereas 'NAVSEL 21' exhibits a horizontal growth habit, thicker trunk, 5R 3/4 skin color, earlier bud burst, and increased inflorescences per cluster.

BRIEF DESCRIPTION OF THE DRAWING

FIG. 1—Shows the form, foliage, and fruit of a 4-year-old 'NAVSEL 20' vine grown in the field in Murcia, Spain. The colors shown are as true as can be reasonably obtained by conventional photographic procedures.

DETAILED BOTANICAL DESCRIPTION

The following detailed description sets forth the distinctive characteristics of 'NAVSEL 20'. The detailed description was obtained between March and November using 4-year-old plants grown in the field in Murcia, Spain. The color references are to the *Munsell Plant Tissue Color Book,* 2012 Edition by Munsell Color.

Classification:
- *Family*.—Vitaceae.
- *Botanical.—Vitis vinifera.*
- *Common name*.—Grapevine.
- *Cultivar name*.—'NAVSEL 20'.

Plant:
- *Plant habit and growth*.—Semi-erect.
- *Age at maturity*.—4 years old.
- *Size* (*at maturity*).—Height: 225 cm. Width: 300 cm.
- *Vigor*.—Medium to high.
- *Productivity*.—Medium.
- *Rootstock*.—Name of rootstock: 1103 Paulsen Rootstock. Age of rootstock at time of grafting: one year old.

Trunk:
- *Size*.—Diameter: 4.3 cm.
- *Shape*.—Straight, cylindrical, irregular.
- *Surface texture*.—Smooth.
- *Bark colour*.—Exterior: 7.5 YR 6/4. Interior: 2.5 YR 4/4.

Canes:
- *Size*.—Diameter: 12 mm. Length: 170 cm.
- *Surface texture*.—Mature cane: smooth. Immature cane: smooth and very slightly ribbed Form (woody shoot cross section form): pith in center with diaphragm at the nodes.
- *Color*.—Mature: 2.5 GY 5/6 at 5 months. Immature: 2.5GY 5/8 at 4 weeks. Dorsal side of internodes: 5R 3/4 at 5 months. Ventral side of internodes: 5GY 5/6 at 5 months. Dorsal side of nodes: 5R 3/4 at 5 months. Ventral side of nodes: 5GY 5/6 at 5 months.
- *Internode length* (*upper mature sun cane*).—17.2 cm (on June 15).
- *Internode width* (*upper mature sun cane*).—8.70 mm (on June 15).
- *Node width*.—12.6 mm (on June 15).

Bud:
- *Bud description*.—Winter bud: color 5YR 4/4; small, rounded, and pointed. Green bud: color 5GY 6/6; no anthocyanin coloration.
- *Time of bud burst*.—50% bud break by March 15.
- *Time of bud leaf burst*.—March 17.

Tendrils:
- *Form*.—Mostly trifid.
- *Size*.—Very long.
- *Length*.—29 cm.
- *Diameter*.—2.5 mm.
- *Texture and distribution of tendril at each node beginning at base*.—Smooth and discontinuous; 0000100000100001000101 (0 means no tendril at that node and 1 means there is tendril at the node).
- *Color*.—Mature: 2.5GY 6/6 at 4 weeks. Immature: 5Y 5/6 at 10 days.
- *Anthocyanin*.—Mature: 7.5YR 5/6. Immature: 2.5Y 5/6.

Growing tips (young shoot):
- *Pubescence*.—Absent.
- *Color*.—2.5GY 6/6.
- *Anthocyanin*.—Present, 5YR 4/4.
- *Shape*.—Fully open.
- *Apex*.—Triangular.
- *Shoot attitude before tying*.—Semi-erect.

Leaves:
- *Shape*.—Orbicular-reniform.
- *Density*.—Medium.
- *Apex*.—Pointed.
- *Base*.—Rounded.
- *Number of lobes*.—5.
- *Depth of upper lateral sinuses of mature leaves*.—Medium.
- *Arrangement of lobes of upper lateral sinuses on mature leaves*.—Strongly overlapped.
- *Margin*.—Irregular teeth.
- *Length of teeth on margin*.—2-10 mm.
- *Shape of teeth on margin*.—Mixture of both sides straight and both sides convex.
- *Texture* (*mature leaf*).—Upper surface: smooth. Lower surface: smooth, very bullated along primary veins.
- *Size*.—Immature: Length: 8 cm at 10 days. Width: 8 cm at 10 days. Mature: Length: 17.8 cm at 4 weeks. Width: 16.4 cm at 4 weeks.
- *Color*.—Immature leaf: Upper surface: 5GY 5/6; anthocyanin 5Y 5/6. Lower surface: 2.5GY 5/6; anthocyanin 5Y 5/4. Mature leaf: Upper surface: 7.5GY 3/4 Lower surface: 5GY 4/4. Autumn coloration: upper surface: 5GY 6/6; lower surface: 5GY 7/6.
- *Venation*.—Pattern: veins on upper leaf are flat; veins on lower leaf are raised. Length of middle vein in mature leaves: 14.25 cm. Color: Upper surface: 7.5YR 5/4. Lower surface: 2.5GY 7/4.
- *Petiolar sinus include general description*.—Half open.
- *Petiole*.—Length: 9.2 cm. Diameter: 3.0 mm. Color: 2.5GY 5/6; anthocyanin 5YR 4/8.

Floral cluster:
- *General description and location*.—Mostly $5^{th}$ or $6^{th}$ node; 15% without shoulders.
- *Quantity of inflorescences per cluster*.—800.
- *Size*.—Length: 13 cm. Width: 10.5 cm (spread); 8.2 cm (hanging).
- *Peduncle length*.—5.6 cm.
- *Inflorescences*.—Hermaphroditic.
- *Stamens*.—Straight, 2.6 mm.
- *Anthers*.—Small and nondescript.
- *Date of bloom*.—Start of bloom, May 6; and 100% bloom, May 15.
- *Pollen amount*.—Sparse.
- *Calyptra*.—5 segments with complete separation.
- *Calyptra color*.—5GY 5/8.

Fruit:
- *Time of year of commercial harvest and shipment*.—Early season, July in Murcia, Spain.

*Keeping quality*.—After 30 days of storage, the variety may show slight symptoms of dehydration of the pedicel and secondary stem. Excellent eating quality.

*Cluster* (*primary bunches*).—General size: medium (550 g tipped and 600 g not tipped). Length (without peduncle): 17 cm tipped and 22 cm not tipped. Width: 12.5 cm (hanging), 16 cm (spread). Density: medium. Peduncle: Length: 6 cm. Diameter: 5.7 mm. Color: 2.5GY 6/6. Number of berries per cluster: 60 tipped and 70 not tipped. Berry: Size: large (10 g). Diameter: 22 mm. Length: 29 mm. Shape: cylindrical. Uniformity: very uniform. Brix content: 21.5° Brix. Skin color: 5RP 3/2. Pedicel: Length: 9.4 mm. Diameter: 1.8 mm. Color: 2.5GY 6/6. Strength of attachment to berry: medium.

*Cluster* (*secondary bunches*).—General size: medium (375 g). Length (without peduncle): 12 cm. Width: 12.5 cm (hanging), 19 cm (spread). Density: medium. Peduncle: Length: 4 cm. Diameter: 4.7 mm. Color: 2.5GY 7/6. Number of berries per cluster: 42. Berry: Size: large (5.5 g). Diameter: 21 mm. Length: 23 mm. Shape: cylindrical. Uniformity: very uniform. Brix content: 21° Brix. Titratable acidity: 0.6%. Color: Skin color: 5RP 3/2. Color of immature berry skin without bloom: 5GY 4/8 (measured at 6 mm diameter). Pedicel: Length: 8.2 mm. Diameter: 1.5 mm. Color: 2.5GY 6/6. Strength of attachment to berry: medium.

Berry flesh:

*Color*.—2.5GY 8/2.

*Juice color*.—5Y 8/4.

*Juice production*.—High, 33% wt/wt.

*Thickness of skin*.—Thin.

*Flavor*.—Neutral.

*Fragrance*.—Neutral.

*Texture*.—Very crisp (51.4 shores; Shore A scale; 53215 Durometer.

*Seeds*.—Seed rudiments not detectable.

*Use*.—Fresh table.

Disease and insect resistance: The disease and insect resistance of this cultivar is typical of its species.

What is claimed is:

1. A new and distinct variety of grapevine plant named 'NAVSEL 20' as shown and described herein.

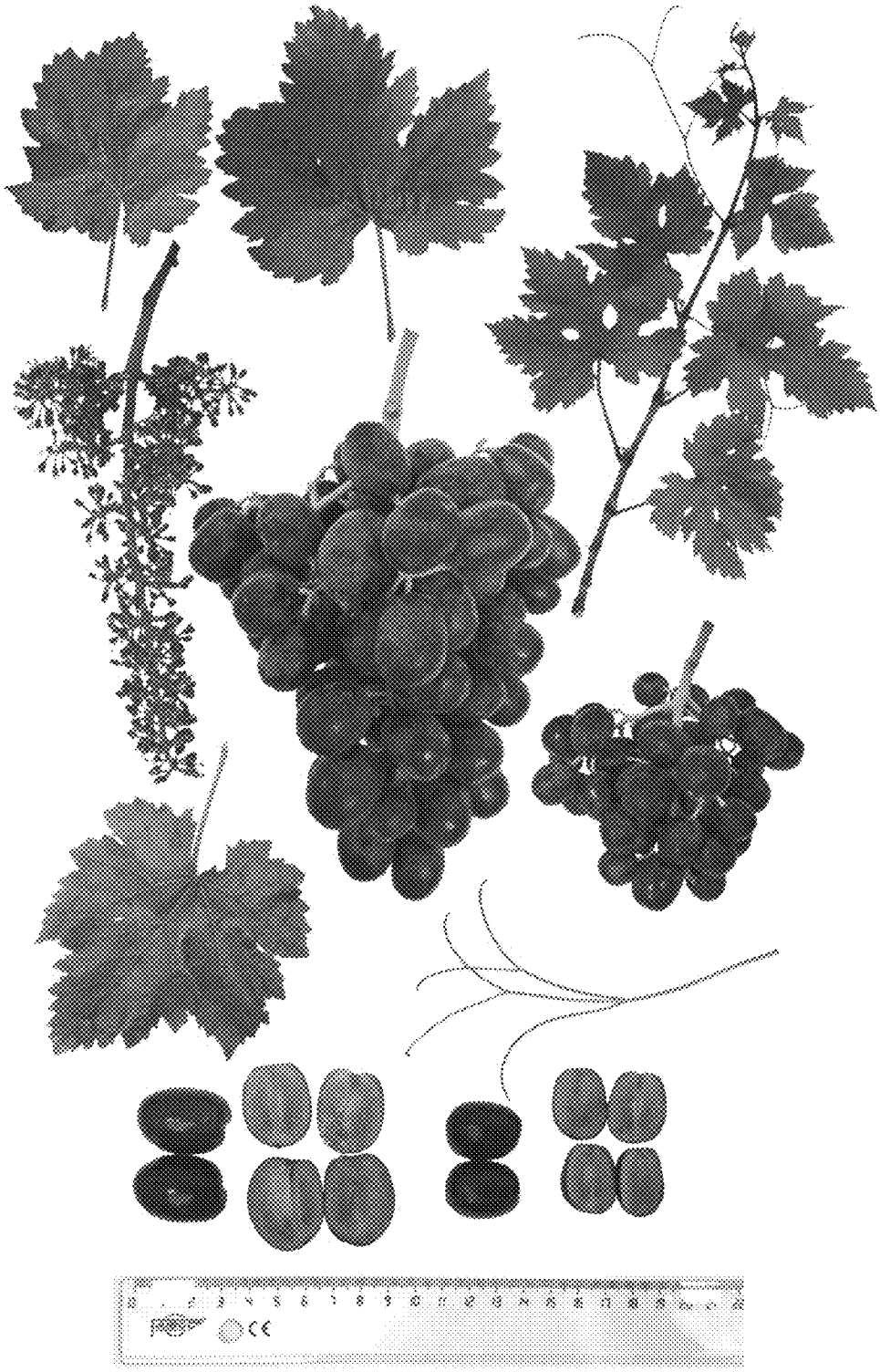

* * * * *